United States Patent
Camenzind et al.

(10) Patent No.: US 7,026,438 B2
(45) Date of Patent: Apr. 11, 2006

(54) LIQUID PHENOLIC SULPHUR-CONTAINING ANTIOXIDANTS

(75) Inventors: Hugo Camenzind, Bern (CH); Paul Dubs, Cham (CH); Roger Martin, Rheinfelden (CH); David Eliezer Chasan, Teaneck, NJ (US); Gunnar Demme, Mahopac, NY (US); James Robbins, Satsuma, AL (US)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 10/723,744

(22) Filed: Nov. 26, 2003

(65) Prior Publication Data

US 2004/0267042 A1   Dec. 30, 2004

Related U.S. Application Data

(60) Provisional application No. 60/430,228, filed on Dec. 2, 2002.

(51) Int. Cl.
*C08G 63/688*   (2006.01)
*C08G 75/00*   (2006.01)

(52) U.S. Cl. ............. 528/360; 528/361; 528/364; 528/373; 524/292; 524/386; 560/60; 252/404

(58) Field of Classification Search ......... 524/292, 524/386; 252/404; 560/60; 528/360, 361, 528/364, 373
See application file for complete search history.

(56) References Cited

U.S. PATENT DOCUMENTS

| | | | |
|---|---|---|---|
| 4,694,099 A | 9/1987 | Ahlfors et al. | 560/75 |
| 5,478,875 A | 12/1995 | Dubs et al. | 524/291 |
| 5,892,097 A | 4/1999 | Ross et al. | 560/75 |

OTHER PUBLICATIONS

Evans et al, Liquid antioxidants as stabilizers, 1995, Chem Abstract 122: 265035.*

* cited by examiner

*Primary Examiner*—Duc Truong
(74) *Attorney, Agent, or Firm*—Tyler A. Stevenson

(57) ABSTRACT

The invention relates to liquid sulphur-containing antioxidants and to compositions comprising them. The novel lubricant compositions comprise the reaction product of a selected group of 5-tert-butyl-4-hydroxy-3-methyl(or tert-butyl)phenyl substituted carboxylic acid esters with thiodiethylene glycol and a mono-hydroxy alcohol with a carbon chain length higher than 4 C-atoms. The novel lubricant compositions are highly resistant to oxidative degradation and are capable of reducing the negative effects of deposits, such as black sludge, in motor combustion engines, particularly spark ignition internal combustion engines.

11 Claims, No Drawings

LIQUID PHENOLIC SULPHUR-CONTAINING ANTIOXIDANTS

This application claims the benefit under 35 USC 119(e) of U.S. provisional application No. 60/430,228, filed Dec. 2, 2002.

The present invention relates to liquid phenolic sulphur-containing antioxidants, to compositions comprising the liquid sulphur-containing antioxidants and to a process for stabilising compositions of matter, particularly lubricants, against oxidative, thermal or light induced degradation.

It is known that additives improve the performance properties of functional fluids, such as lubricants, particularly mineral oils or synthetic or semi-synthetic oils. Particularly additives are highly desirable which reduce the formation of oxidative degradation products and promote the stability of lubricants.

The compound of the formula

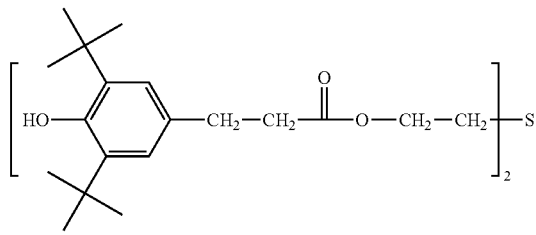

Irganox® 1035 (Registered Trademark of Ciba Specialty Chemicals), which is a solid dimeric sulphur-containing ester type phenolic antioxidant, is particularly preferred as an antioxidative agent in lubricant compositions in view of its low volatility and high antioxidative efficiency. A disadvantage of antioxidative agents of this type is their low solubility in oils. In addition, they are solids with melting points above room temperature (IRGANOX 1035: >40° C.). Therefore, liquid additives of high oil solubility are preferred for the formulation of lubricant mixtures and so-called additive packages.

EP-A-0 565 487 discloses lubricant compositions of liquid antioxidants of low volatility consisting of the reaction product of a phenolic antioxidant, e.g. 3-(3,5-di-tert-butyl-4-hydroxyphenyl)-propionic acid methyl ester, with a polyol, e.g. thiodiethylene glycol, and a glyceride, such as sun-flower or coconut oil.

Novel lubricant compositions have now been found that possess advantageous antioxidative properties as compared with the prior art compositions. The novel lubricant compositions comprise the reaction product of at least one phenolic antioxidant from the selected group of 5-tert-butyl-4-hydroxy-3-methyl (or 3-tert-butyl)-phenyl substituted carboxylic acid esters with a thiodiethylene glycol and a monohydroxy alcohol with a carbon chain length higher than 4 C-atoms. The novel lubricant compositions are highly resistant to oxidative degradation and are capable of reducing the negative effects of deposits in combustion engines, particularly spark ignition internal combustion engines.

The present invention relates to a product obtainable by reacting a) At least one compound

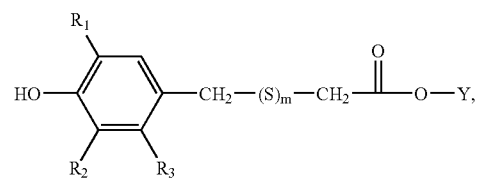

wherein
one of $R_1$ and $R_2$ independently of one another represents hydrogen or a substituent selected from the group consisting of $C_1$–$C_{18}$alkyl, phenyl, $(C_1$–$C_4$alkyl$)_{1-3}$phenyl, phenyl-$C_1$–$C_3$alkyl, $(C_1$–$C_4$alkyl$)_{1-3}$phenyl-$C_1$–$C_3$alkyl, $C_5$–$C_{12}$cycloalkyl and $(C_1$–$C_4$alkyl$)_{1-3}$ $C_5$–$C_{12}$cycloalkyl;
and the other one represents a substituent selected from the group consisting of $C_1$–$C_{18}$alkyl, phenyl, $(C_1$–$C_4$alkyl$)_{1-3}$phenyl, phenyl-$C_1$–$C_3$alkyl, $(C_1$–$C_4$alkyl$)_{1-3}$phenyl-$C_1$–$C_3$alkyl, $C_5$–$C_{12}$cycloalkyl and $(C_1$–$C_4$alkyl$)_{1-3}$ $C_5$–$C_{12}$cycloalkyl;
$R_3$ represents hydrogen or methyl;
Y represents hydrogen or $C_1$–$C_6$alkyl; and
m represents zero or 1; with b) At least one compound $$R_4\text{—OH} \qquad (II),$$

wherein $R_4$ represents $C_4$–$C_{25}$alkyl; and;

c) At least one compound

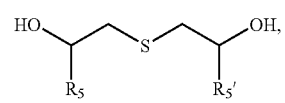

wherein $R_5$ and $R_5'$ independently of one another represent hydrogen or $C_1$–$C_6$alkyl.

The products according to the instant invention obtainable by reacting components a), b) and c) are, for example, valuable antioxidants against oxidative, thermal or actinic degradation of any organic compositions of matter. Such compositions are, for example, natural or synthetic polymers, or functional fluids, such as lubricant compositions, hydraulic fluids or metalworking fluids.

Lubricant compositions that contain the product defined above are characterised by their excellent antioxidative properties, which can be demonstrated in various generally accepted tests such as Deposit and Oxidation Panel Test (DOPT) and High Pressure Differential Scanning Calorimetry (HPDSC).

The products according to the instant invention, obtainable by reacting components a), b) and c), have excellent oxidative stability and are particularly suitable as additives in lubricant compositions, particularly for use in internal combustion engines, such as spark-ignition internal combustion engines, popularly known as Otto engines, or self-ignition internal combustion engines, popularly known as Diesel engines.

The products, as defined above, are particularly suitable for formulating lubricant compositions and blending so-called additive packages, which remain clear and homogenous liquids on storage at room temperature. The lubricant compositions are particularly suitable as motor oils, which correspond to the API (American Petroleum Institute) and the CCMC (Committee of Common Market Automobile Constructors) classifications.

The definitions and general terms used in the description of the present invention preferably have the following meanings:

Component a)

The various alkyl groups defined above of different chain length comprise saturated linear or, where possible, branched hydrocarbon groups, particularly $C_1$–$C_6$alkyl, e.g. methyl, ethyl, isopropyl, n-butyl, isobutyl, tert-butyl, n-pentyl, neopentyl, isopentyl, tert-pentyl, n-hexyl, 2-ethylbutyl, 1-methylpentyl or 1,3-dimethylbutyl. Alkyl groups of higher chain length are, e.g. 1-methylpentyl, 1,3-dimethylbutyl, n-heptyl, 3-heptyl, 1-methylhexyl, isoheptyl, n-octyl, 2-ethylhexyl, 1,1,3,3-tetramethylbutyl, 1-methylheptyl, n-nonyl or 1,1,3-trimethylhexyl, as well as $C_{10}$–$C_{25}$alkyl, particularly straight chained $C_{10}$–$C_{25}$alkyl, e.g. n-decyl, n-dodecyl, n-tetradecyl, n-hexadecyl, n-octadecyl, icosyl, henicosyl or docosyl, or branched $C_{10}$–$C_{25}$alkyl, e.g. 1-methylundecyl, 2-n-butyl-n-octyl, isotridecyl, 2-n-hexyl-n-decyl or 2-n-octyl-n-dodecyl, or higher homologues thereof.

($C_1$–$C_4$Alkyl)$_{1-3}$phenyl is, for example, 2- or 4-tolyl, 2,5- or 2,6-xylyl, mesityl, 2- or 4-ethylphenyl, 2,4- or 2,6-diethylphenyl, 4-cumenyl, 2-tert-butyl-6-methylphenyl or 2,6-bis-tert-butyl.

Phenyl-$C_1$–$C_3$alkyl is, for example, phenyl attached to $C_1$–$C_3$alkyl in 1-, 2- or 3-position, e.g. 2-phenylethyl, particularly benzyl.

($C_1$–$C_4$Alkyl)$_{1-3}$phenyl-$C_1$–$C_3$alkyl is one of the above mentioned ($C_1$–$C_4$alkyl)$_{1-3}$phenyl attached to $C_1$–$C_3$alkyl in 1-, 2- or 3-position, e.g. 2-tert-butyl-6-methylbenzyl or 2,6-bis-tert-butyl-phenyl.

$C_5$–$C_{12}$Cycloalkyl is, for example, cyclopentyl or cyclohexyl.

($C_1$–$C_4$Alkyl)$_{1-3}$$C_5$–$C_{12}$cycloalkyl is one of the above-mentioned $C_5$–$C_{12}$cycloalkyl groups substituted with 1–3 $C_1$–$C_4$alkyl, e.g. 2- or 4-methylcyclohexyl, 2,6-dimethylcyclohexyl, 2,4,6-trimethylcyclohexyl or 4-tert-butylcyclohexyl.

In a compound (I), the numeral m represents zero or one. In the event that m represents zero, the direct bond is defined.

A particularly preferred group of compounds (I), wherein m is zero, is represented by the general formula:

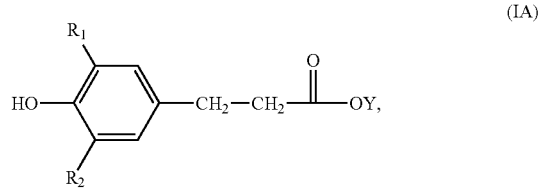

(IA)

wherein one of $R_1$ and $R_2$ represents methyl or tert-butyl and the other one represents tert-butyl and Y represents hydrogen or methyl.

Component b)

$R_4$ in a compound (II) represents $C_4$–$C_{25}$alkyl, particularly n-butyl, n-pentyl, neopentyl, isopentyl, n-hexyl, 2-ethylbutyl, 1-methylpentyl, 1,3-dimethylbutyl, n-heptyl, 3-heptyl, 1-methylhexyl, isoheptyl, n-octyl, 2-ethylhexyl, 1,1,3,3-tetramethylbutyl, 1-methylheptyl, n-nonyl or 1,1,3-trimethylhexyl, as well as $C_{10}$–$C_{25}$alkyl, particularly branched $C_1$–$C_{25}$alkyl, e.g. 1-methylundecyl, 2-n-butyl-n-octyl, isotridecyl, 2-n-hexyl-n-decyl or 2-n-octyl-n-dodecyl, or higher homologues thereof.

Component c)

In a compound (III) $R_5$ and $R_5'$ independently of one another represent hydrogen or $C_1$–$C_6$alkyl. A particularly preferred compound is thiodiethylene glycol.

A preferred embodiment of the invention relates to a product obtainable by reacting a) At least one compound (I), wherein one of $R_1$ and $R_2$ represents methyl or tert-butyl and the other one of $R_1$ and $R_2$ represents tert-butyl; $R_3$ represents hydrogen; Y represents $C_1$–$C_6$alkyl; and m represents zero or one; and b) At least one compound (II), wherein $R_4$ represents $C_5$–$C_{18}$alkyl; and;

c) At least one compound (III), wherein $R_5$ and $R_5'$ represent hydrogen.

A particularly preferred embodiment of the invention relates to a product obtainable by reacting a) At least one compound (I), wherein one of $R_1$ and $R_2$ represents methyl or tert-butyl and the other one of $R_1$ and $R_2$ represents tert-butyl; $R_3$ represents hydrogen; Y represents methyl and m represents zero; and b) At least one compound (II), wherein $R_4$ represents $C_5$–$C_{18}$alkyl; and;

c) At least one compound (III), wherein $R_5$ and $R_5'$ represent hydrogen.

A highly preferred embodiment of the invention relates to a product obtainable by reacting a) A mixture comprising a compound (I), wherein $R_1$ and $R_2$ represent tert-butyl; $R_3$ represents hydrogen; Y represents methyl and m represents zero; and a compound (I), wherein one of $R_1$ and $R_2$ represents methyl and the other one tert-butyl; $R_3$ represents hydrogen; Y represents methyl and m represents zero; and b) At least one compound (II), wherein $R_4$ represents $C_5$–$C_{18}$alkyl; and;

c) At least one compound (III), wherein $R_5$ and $R_5'$ represent hydrogen.

Another embodiment of the invention relates to a product obtainable by reacting the component a) with a surplus of the molar quantities of the combined components b) and c). In a preferred embodiment the molar quantity of a) is smaller than or equal to the sum of the molar quantities of b) and c), provided that the molar quantity of c) is twice with regard to b), i.e. a) [b)+2c)].

In another preferred embodiment the components a), b) and c) are reacted in a molar quantity ratio of 2.0:1.0:1.0 to 10.0:8.0:1.0. A molar quantity ratio of 2.0:1.0:1.0 to 5.0:4.0:1.0 is particularly preferred.

The products according to the invention preferably comprise the active group

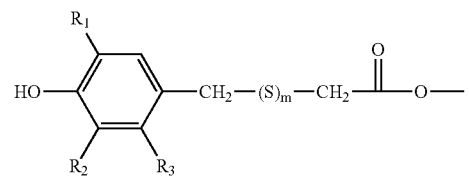

in a percentage of 30.0 to 80.0% by weight, particularly 50.0 to 80.0% by weight.

Another embodiment of the invention relates to a process for preparing a liquid mixture of phenolic sulphur-containing antioxidants, which comprises reacting a) At least one compound (I), wherein $R_1$, $R_2$, $R_3$, Y and m are as defined above, with b) At least one compound (II), wherein $R_4$ is as defined above; and c) At least one compound (III), wherein $R_5$ and $R_5'$ are as defined above.

A preferred embodiment of the process comprises reacting the ester component a) with components b) and c), provided that at least a slight, particularly a significant, molar excess of hydroxy groups is present in the reaction mixture.

The three components a), b) and c) can be reacted with each other to give the products α-cording to the invention in any desired sequence. Preferably, component a) is reacted simultaneously with component b) and component c). The process is preferably carried out in the presence of a suitable catalyst, e.g. so-called Lewis bases or acids.

Suitable Lewis bases are metal hydrides, alkylides, arylides, hydroxides, alcoholates, phenolates, amides or carboxylates.

Examples of preferred metal hydrides are lithium, sodium, potassium or calcium hydride.

An example of a preferred metal alkylide is n-butyl-lithium.

An example of a preferred metal arylide is phenyllithium.

Examples of preferred metal hydroxides are lithium, sodium, potassium or calcium hydroxide.

Examples of preferred metal alcoholates are lithium, sodium or potassium methanolate (=methylate) or ethanolate (=ethylate).

Examples of preferred metal phenolates are sodium or potassium phenolate.

Examples of preferred metal amides are sodium or lithium amide.

Examples of preferred carboxylates are sodium or calcium acetate or sodium benzoate.

Examples of suitable Lewis acids are represented by the formulae:

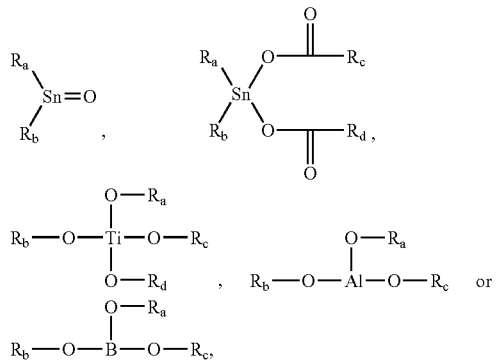

wherein $R_a$, $R_b$, $R_c$, and $R_d$ independently of one another represent $C_1$–$C_{18}$alkyl or phenyl.

$C_1$–$C_8$Alkyl is preferred. A particularly preferred Lewis acid is dibutyltin oxide or aluminium isopropoxide.

The catalyst is added to components a), b) and c) in a preferred amount of 0.05 to 10.0% by weight, preferably in an amount of 0.1 to 5.0% by weight. The addition of 0.5 to 2.0% by weight is particularly preferred. The addition of the catalyst in an inert solvent, such as a polar protic or non-protic solvent, e.g. methanol or ethanol, is optional.

The reaction of components a), b) and c) in a high-boiling solvent, for example a non-polar aprotic solvent, e.g. xylene, is optional. The preferred reaction temperature range is between 130 and 250° C. A particularly preferred reaction temperature range is between 130 and 190° C.

Components a), b) and c) are known and commercially available or can be prepared from known and commercially available compounds by applying known methods.

The invention relates also to the use of a mixture of the individual components a), b) and c), preferably in the mentioned concentration, as additives in motor oils, turbine oils, gear oils, hydraulic fluids, metal-working fluids or lubricating greases.

The invention relates in particular to the use of the product obtainable by reacting the individual components a), b) and c), preferably in the mentioned concentration, as additives in motor oils, turbine oils, gear oils, hydraulic fluids, metal-working fluids or lubricating greases.

Another embodiment of the invention relates to a process for stabilising the composition of matter subject to oxidative, thermal or light induced degradation, which comprises adding to said composition of matter at least one product as defined above.

The invention likewise relates to a process for protection against corrosion or oxidative degradation of metals, which are in contact with functional fluids, wherein the reaction product defined further above, obtainable by reacting the individual components a), b) and c), is added to the functional fluid.

Another embodiment of the invention relates to a composition comprising

A) A product as defined above; and

B) A functional fluid subject to oxidative, thermal or light induced degradation.

The term functional fluid includes aqueous, partially aqueous and non-aqueous fluids, particular base oils of lubricating viscosity, which can be used for the preparation of greases, metal working fluids, gear fluids and hydraulic fluids.

The compositions according to the invention preferably comprise 0.01 to 5.0% by weight, in particular 0.02 to 1.0% by weight, of the reaction product, based on the weight of the functional fluid.

Examples of aqueous functional fluids are industrial cooling water, filling compositions of a water conditioning plant, steam generation systems, sea water evaporation systems, sugar evaporation systems, irrigation systems, hydrostatic boilers and heating systems or cooling systems having a closed circulation.

Examples of suitable partially aqueous functional fluids are hydraulic fluids based on aqueous polyglycol/polyglycol ether mixtures or glycol systems, water-in-oil or oil-in-water systems and engine cooling systems based on aqueous glycol.

Examples of non-aqueous functional fluids are fuels, e.g. hydrocarbon mixtures comprising mineral oil fractions which are liquid at room temperature and are suitable for use in internal combustion engines, e.g. internal combustion engines with external (petrol engines) or internal ignition (diesel engines), e.g. petrol having different octane contents (regular grade or premium grade petrol) or diesel fuel, and lubricants, hydraulic fluid, metal working fluid, engine coolants, transformer oil and switchgear oil.

Non-aqueous functional fluids are preferred, in particular base oils of lubricating viscosity, which can be used for the preparation of greases, metal working fluids, gear fluids and hydraulic fluids.

Suitable greases, metal working fluids, gear fluids and hydraulic fluids are based, for example, on mineral or synthetic oils or mixtures thereof. The lubricants are familiar to a person skilled in the art and are described in the relevant literature, such as, for example, in *Chemistry and Technology of Lubricants*; Mortier, R. M. and Orszulik, S. T. (Editors); 1992 Blackie and Son Ltd. for GB, VCH-Publishers N.Y. for U.S., ISBN 0-216-92921-0, cf. pages 208 et seq. and 269 et seq.; in *Kirk-Othmer Encyclopedia of Chemical Technology*, Fourth Edition 1969, J. Wiley & Sons, New York, Vol. 13, page 533 et seq. (Hydraulic Fluids); *Performance Testing of Hydraulic Fluids*; R. Tourret and E. P. Wright, Hyden & Son Ltd. GB, on behalf of The Institute of Petroleum London, ISBN 0 85501 317 6; *Ullmann's Encyclopedia of Ind. Chem.*, Fifth Completely Revised Edition, Verlag Chemie, D E-Weinheim, VCH-Publishers for U.S., Vol. A 15, page 423 et seq. (Lubricants), Vol. A 13, page 165 et seq. (Hydraulic Fluids).

A particularly preferred embodiment of the invention relates to a lubricant composition comprising
A) A product as defined above; and
B) A base oil of lubricating viscosity.

The lubricants are in particular oils and greases, for example based on mineral oil or vegetable and animal oils, fats, tallow and wax or mixtures thereof. Vegetable and animal oils, fats, tallow and wax are, for example, palm kernel oil, palm oil, olive oil, colza oil, rapeseed oil, linseed oil, soy bean oil, cotton wool oil, sunflower oil, coconut oil, maize oil, castor oil, walnut oil and mixtures thereof, fish oils, and chemically modified, e.g. epoxidised or sulphoxidised, forms or forms prepared by genetic engineering, for example soy bean oil prepared by genetic engineering.

Examples of synthetic lubricants include lubricants based on aliphatic or aromatic carboxylic esters, polymeric esters, polyalkylene oxides, phosphoric acid esters, poly-α-olefins or silicones of the diester of a dibasic acid with a monohydric alcohol, e.g. dioctyl sebacate or dinonyl adipate, of a triester of trimethylolpropane with a monobasic acid or with a mixture of such acids, e.g. trimethylolpropane tripelargonate, trimethylolpropane tricaprylate or mixtures thereof, of a tetra ester of pentaerythritol with a monobasic acid or with a mixture of such acids, e.g. pentaerythrityl tetracaprylate, or of a complex ester of monobasic and dibasic acids with polyhydric alcohols, e.g. a complex ester of trimethylolpropane with caprylic and sebacic acid or of a mixture thereof. Particularly suitable in addition to mineral oils are, for example, poly-α-olefins, ester-based lubricants, phosphates, glycols, polyglycols and polyalkylene glycols and mixtures thereof with water.

Said lubricants or mixtures thereof can also be mixed with an organic or inorganic thickener (base fat). Metal working fluids and hydraulic fluids can be prepared on the basis of the same substances as described above for the lubricants. These are frequently also emulsions of such substances in water or other fluids.

The invention relates also to a method of improving the performance properties of lubricants, which comprises adding to the lubricant at least one product as defined above. The lubricant compositions, e.g. greases, gear fluids, metal working fluids and hydraulic fluids, may additionally contain further additives, which are added to improve further their performance properties. These include: other antioxidants, metal deactivators, rust inhibitors, viscosity index improvers, pour-point depressants, dispersants, detergents, high pressure additives and antiwear additives. Such additives are added in customary amounts, each in the range from 0.01 to 10.0% by weight. Examples of further additives are listed below:

1. Phenolic antioxidants
1.1. Alkylated monophenols: 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear nonylphenols or nonylphenols which are branched in the side chain, e.g. 2,6-dinonyl-4-methylphenol, 2,4-dimethyl-6-(1'-methylundec-1'-yl)-phenol, 2,4-dimethyl-6-(1'-methylheptadec-1'-yl)-phenol, 2,4-dimethyl-6-(1'-methyltridec-1'-yl)-phenol and mixtures thereof
1.2. Alkylthiomethylphenols: 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol
1.3. Hydroquinones and alkylated hydroquinones: 2,6-di-tert-butyl-4-methoxyphenol, 2,5-di-tert-butyl-hydroquinone, 2,5-di-tert-amyl-hydroquinone, 2,6-diphenyl-4-octadecyl-oxyphenol, 2,6-di-tert-butyl-hydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate
1.4. Tocopherols: α-, β-, γ or δ-tocopherols and mixtures thereof (vitamin E)
1.5. Hydroxylated thiodiphenyl ethers: 2,2'-thiobis(6-tert-butyl-4-methylphenol), 2,2'-thiobis(4-octylphenol), 4,4'-thiobis(6-tert-butyl-3-methylphenol), 4,4'-thiobis-(6-tert-butyl-2-methylphenol), 4,4'-thiobis(3,6-di-sec-amylphenol), 4,4'-bis(2,6-dimethyl-4-hydroxyphenyl)disulphide
1.6. Alkylidene bisphenols: 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methyl-benzyl)-6-tert-butyl-4-methyl-phenyl]terephthalate, 1,1-bis(3,5-dimethyl-2-hydroxyphenyl)-butane, 2,2-bis(3,5-di-tert-butyl-4-hydroxyphenyl)-propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane
1.7. O-, N- and S-benzyl compounds: 3,5,3',5'-tetra-tert-butyl-4,4'-dihydroxydibenzyl ether, octadecyl 4-hydroxy-3,5-dimethylbenzylmercaptoacetate, tridecyl-4-hydroxy-3,5-di-tert-butylbenzylmercaptoacetate, tris(3,5-di-tertbutyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulphide, isooctyl 3,5-di-tert-butyl-4-hydroxybenzylmercaptoacetate 1.8. Hydroxybenzylated malonates: dioctadecyl 2,2-bis(3,5-di-tert-butyl-2-hydroxybenzyl)malonate, dioctadecyl 2-(3-tert-butyl-4-hydroxy-5-methylbenzyl)malonate, didodecyl mercaptoethyl-2,2-bis(3,5-di-tert-butyl-4-hydroxybenzyl)malonate, di-[4-(1,1,3,3-tetramethylbutyl)-phenyl]-2,2-bis(3,5-di-tert-butyl-4-hydroxybenzyl)malonate 1.9. Hydroxybenzyl aromatics: 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol 1.10. Triazine compounds: 2,4-bisoctylmercapto-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate 1.11. Acylaminophenols: 4-hydroxylauranilide, 4-hydroxystearanilide, octyl N-(3,5-di-tert-butyl-4-hydroxyphenyl) carbamate 1.12. Esters of beta-(3,5-di-tert-butyl-4-hydroxyphenyl)-propionic acid with monohydric or polyhydric alcohols, e.g. with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalamide, 3-thiaundecanol, 3-thiapentadecanol, trimethylhexanediol, trimethylolpropane, 4-hydroxymethyl-1-phospha-2,6,7-trioxabicyclo[2.2.2]octane 1.13. Esters of beta-(5-tert-butyl-4-hydroxy-3-methylphenyl)propionic acid (with monohydric or polyhydric alcohols), e.g. with methanol, ethanol, n-octanol, isooctanol, octadecanol, 1,6-hexanediol, 1,9-nonanediol, ethylene glycol, 1,2-propanediol, neopentylglycol, thiodiethylene glycol, diethylene glycol, triethylene glycol, pentaerythritol, tris(hydroxyethyl)isocyanurate, N,N'-bis(hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2]octane 1.14. Esters of beta-(3,5-dicyclohexyl-4-hydroxyphenyl) propionic acid with monohydric or polyhydric alcohols, e.g. the alcohols stated under 1.13.

1.15. Ester of 3,5-di-tert-butyl-4-hydroxyphenylacetic acid with monohydric or polyhydric alcohols, e.g. the alcohols stated under 1.13.

1.16. Amides of beta-(3,5-di-tert-butyl-4-hydroxyphenyl) propionic acid. e.g. N,N'-bis(3,5-di-tert-butyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxy-phenylpropionyl)hydrazine 1.17. Ascorbic acid (vitamin C)

1.18. Amine antioxidants: N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphth-2-yl)-p-phenylenediamine, N-isopropyl-N'-phenyl-p-phenylenediamine, N-(1,3-dimethyl-butyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphonamido) diphenylamine, N,N'-dimethyl-N,N'-di-sec-butyl-p-phenylenediamine, diphenylamine, N-allyidiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, e.g. p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-di-[(2-methyl-phenyl)-amino] ethane, 1,2-di-(phenylamino)-propane, (o-tolyl)biguanide, di-[4-(1',3'-dimethylbutyl)phenyl]amine, tert-octylated N-phenyl-1-naphthylamine, mixture of mono- and dialkylated tert-butyl/tert-octyldiphenylamines, mixture of mono- and dialkylated nonyldiphenylamines, mixture of mono- and dialkylated dodecyidiphenylamines, mixture of mono- and dialkylated isopropyl/isohexyldiphenylamines, mixtures of mono- and dialkylated tert-butyldiphenylamines, 2,3-dihydro-3,3-dimethyl-4H-1,4-benzothiazine, phenothiazine, mixture of mono- and dialkylated tert-butyl tert-octylphenothiazines, mixture of mono- and dialkylated tert-octylphenothiazines, N-allyl-phenothiazine, N,N,N',N'-tetraphenyl-1,4-diaminobut-2-ene, N,N-bis-(2,2,6,6-tetramethylpiperidin-4-yl)-hexamethylenediamine, bis-(2,2,6,6-tetramethylpiperidin-4-yl)sebacate, 2,2,6,6-tetramethylpiperidin-4-one, 2,2,6,6-tetramethylpiperidin-4-ol 2. Further antioxidants: aliphatic or aromatic phosphites, esters of thiodipropionic acid or thiodiacetic acid or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane 3. Further metal deactivators, e.g. for copper:

3.1 Benzotriazoles and derivatives thereof: 2-mercaptobenzotriazole, 2,5-dimercaptobenzotriazole, 4- or 5-alkylbenzotriazoles (e.g. tolutriazole) and derivatives thereof, 4,5,6,7-tetrahydrobenzotriazole, 5,5'-methylenebisbenzotriazole; Mannich bases of benzotriazole or tolutriazole, such as 1-[di(2-ethylhexylaminomethyl)]tolutriazole and 1-[di(2-ethylhexylaminomethyl)]benzotriazole; alkoxyalkylbenzotriazoles, such as 1-(nonyloxymethyl)-benzotriazole, 1-(1-butoxyethyl)benzotriazole and 1-(1-cyclohexyloxybutyl)tolutriazole 3.2 1,2,4-Triazoles and derivatives thereof: 3-alkyl (or aryl)-1,2,4-triazoles, Mannich bases of 1,2,4-triazoles, such as 1-[di(2-ethylhexyl)aminomethyl]-1,2,4-triazole; alkoxyalkyl-1,2,4-triazoles, such as 1-(1-butoxyethyl)-1,2,4-triazole; acylated 3-amino-1,2,4-triazoles 3.3 Imidazole derivatives: 4,4'-methylenebis(2-undecyl-5-methylimidazole), bis[(N-methyl)imidazol-2-yl]carbinol octyl ether 3.4 Sulphur-containing heterocyclic compounds: 2-mercaptobenzothiazole, 2,5-dimercapto-1,3,4-thiadiazole, 2,5- dimercaptobenzothiadiazole and derivatives thereof; 3,5-bis[di-(2-ethylhexyl)aminomethyl]-1,3,4-thiadiazolin-2-one 3.5 Amino compounds: Salicylidenepropylenediamine, salicylaminoguanidine and salts thereof 4. Corrosion inhibitors 4.1. Organic acids, their esters, metal salts, amine salts and anhydrides: e.g. alkyl- and alkenylsuccinic acids and partial esters thereof with alcohols, diols or hydroxycarboxylic acids, partial amides of alkyl- and alkenylsuccinic acids, 4-nonylphenoxyacetic acid, alkoxy- and alkoxyethoxycarboxylic acids, such as dodecyloxyacetic acid, dodecyloxy(ethoxy)acetic acid and amine salts thereof, and furthermore N-oleoylsarcosine, sorbitan monooleate, lead naphthenate, alkenylsuccinic anhydrides, e.g. dodecenylsuccinic anhydride, 2-(2-carboxyethyl)-1-dodecyl-3-methylglycerol and salts thereof, in particular sodium salts and triethanolamine salts 4.2. Nitrogen-containing compounds:

4.2.1. Tertiary aliphatic and cycloaliphatic amines and amine salts of organic and inorganic acids, e.g. oil-soluble alkylammonium carboxylates, and furthermore 1-[N,N-bis-(2-hydroxyethyl)amino]-3-(4-nonylphenoxy)propan-2-ol 4.2.2. Heterocyclic compounds, e.g. substituted imidazolines and oxazolines, e.g. 2-heptadecenyl-1-(2-hydroxyethyl)-imidazoline 5. Sulphur-containing compounds, barium dinonylnaphthalenesulphonates, calcium petroleum sulphonates, alkylthio-substituted aliphatic carboxylic acids, esters of aliphatic 2-sulphocarboxylic acids and salts thereof 6. Viscosity index improvers: polyacrylates, polymethacrylates, vinylpyrrolidone/methacrylate copolymers, polyvinylpyrrolidiones, polybutenes, olefin copolymers, styrene/acrylate copolymers, polyethers 7. Pour point depressants: poly(meth)acrylates, ethylene-vinyl acetate copolymers, alkyl polystyrenes, fumarate copolymers, alkylated naphthalene derivatives 8. Dispersants/Surfactants: polybutenylsuccinamides or polybutenylsuccinimides, polybutenylphosphonic acid derivatives, basic magnesium, calcium and barium sulphonates and phenolates 9. High pressure and antiwear additives: sulphur- and halogen-containing compounds, e.g. chlorinated paraffins, sulphonated olefins or vegetable oils (soy bean oil, rapeseed oil), alkyl or aryl di- or trisulphides, benzotriazoles or derivatives thereof, such as bis (2-ethylhexyl)aminomethyl tolutriazoles, dithiocarbamates, such as methylenebisdibutyl dithiocarbamate, derivatives of 2-mercaptobenzothiazole, such as 1-[N,N-bis(2-ethylhexyl)-aminomethyl]-2-mercapto-1H-1,3-benzothiazole, derivatives of 2,5-dimercapto-1,3,4-thiadiazole, such as 2,5-bis(tert-nonyldithio-)-1,3,4-thiadiazole 10. Substances for reducing the coefficient of friction: lard oil, oleic acid, tallow, rapeseed oil, and sulphurised fats, amines. Further examples are stated in EP-A-0 565 487

11. Special additives for use in water/oil metal processing and hydraulic fluids:

11.1 Emulsifiers: petroleum sulphonates, amines, such as polyoxyethylated fatty amines, non-ionic surface-active substances 11.2 Buffers: alkanolamines 11.3 Biocides: triazines, thiazolinones, trisnitromethane, morpholine, sodium pyridinethiol 11.4 Processing speed improvers: calcium sulphonates and barium sulphonates.

Said components can be admixed to the lubricant composition in a manner known per se. It is also possible to prepare a concentrate or a so-called additive package, which can be diluted to the concentrations of use for the corresponding lubricant according to the technical requirements.

EXAMPLES

Abbreviations:
AO antioxidants
h hour(s)
min minute(s)
bp boiling point
LC liquid chromatography
TAN total acid number [mg KOH/g]
Visc Viscosity increase Example 1

6.02 g (0.016 mol) lithium methylate (10% in methanol) are added to a mixture of 182.22 g (0.623 mol) 3-(3,5-di-t-butyl-4-hydroxyphenyl)-propionic acid methyl ester, 143.62 g (0.574 mol) 3-(3-t-butyl-4-hydroxy-5-methylphenyl)-propionic acid methyl ester, 77.75 g (0.597 mol) iso-octanol (Exxal®8) and 39.59 g (0.324 mol) thiodiethylene glycol. The mixture is stirred for 6 h at 170–180° C. under reduced pressure. After cooling to room temperature the raw product is dissolved in 300 ml petroleum ether (b.p. 60–90° C.), neutralised with some aqueous citric acid and washed with water. After evaporating the solvent under reduced pressure and drying to-constant weight in vacuo a yellowish oil is obtained.

Refractive index of $n_D^{20}$: 1.5157; Elemental Analysis: C: 72.77, H: 9.85, S: 2.62 [%, found]; LC: 55.3% phenolic monoesters, 36.1% phenolic diester of thiodiethanol, 3.3% phenolic monoesters of thiodiethanol, 2.9% phenolic methyl esters.

Example 2

1.71 g (6.9 mmol) Manalox®130 catalyst (85% alumium isopropoxide in petroleum distillates) are added at 95–100° C. to a pre-dried mixture of 292.4 g (1.0 mol) 3-(3,5-di-t-butyl-4-hydroxy-phenyl)-propionic acid methyl ester, 68.6 g (0.528 mol) iso-octanol (EXXAL 8) and 30.0 g (0.246 mol) thiodiethylene glycol. The mixture is stirred under reduced pressure for 6 h at 158–160° C. and at 180–182° C. for an additional 6–8 h. After cooling to 95° C., 12.0 g Filtrol® or Engelhard Grade 13 clay is added. The temperature is increased to 120° C. under reduced pressure. After 30 min the content is filtered (2.0 g pre-coat of Grade 13 clay on 5μ filter pad) under pressure at 120° C. and a light yellowish oil is obtained.

LC: 54.0–57.0% phenolic monoesters, 38.0–40.0% phenolic diesters of thiodiethanol, 0.5–0.6% phenolic monoester of thiodiethanol, 3.0–3.5% phenolic methyl esters.

Example 3

This example illustrates the performance of one-step synthesis liquid phenolic sulphur-containing antioxidants [Examples 1 and 2] as stabilisers in motor oils.

3.1 ASTM D 4636: Standard test for corrosiveness and oxidation stability of hydraulic oils, aircraft turbine engine lubricants, and other highly refined oils.

To test the antioxidant performance of a test composition containing liquid phenolic sulphur-containing additives, an aging test in neat polyalphaolefin (PAO, Durasyn®) synthetic oil is carried out for 72 h at 191° C. with a flow of 5 l air per h in the presence of five metal test specimen of Fe, Ag, Al, Mg and Cu. After the conclusion of the test the condition of the aged oil is assessed by measuring the acid number and the percent amount of viscosity increase, the sludge generated and the corrosion of the metal test specimen. The results are reported in Table 1.

TABLE 1

| | AO Composition Tested | | | | |
|---|---|---|---|---|---|
| | Test Composition 1 | Test Composition 2 | Ref. 1* | Ref. 2* | Ref. 3* |
| Components | | | | | |
| DURASYN 166 | Balance | Balance | Balance | Balance | Balance |
| IRGANOX L57[1)] | 0.3 | 0.3 | 0.3 | 0.3 | 0.3 |
| Irgamet ® 39[2)] | 0.1 | 0.1 | 0.1 | 0.1 | 0.1 |
| IRGANOX L135[3)] | | | 0.3 | | 0.127 |
| IRGANOX 1035[4)] | | | | 0.3 | 0.138 |
| IRGANOX 1300[5)] | | | | | 0.035 |
| Example 1 | 0.3 | | | | |
| Example 2 | | 0.3 | | | |
| Results | | | | | |
| Δ TAN [mg KOH/g] | 6.8 | 3.0/4.8 | 6.5 | 3.4/2.6 | 3.2 |
| Δ Visc 40° C. [%] | 23.3 | 25.8/23.6 | 51.7 | 10.5/21.1 | 17.8 |
| Sludge [mg/100 ml] | 19.2 | 9.8/14.8 | 12.6 | 72.1/30.3 | 61.7 |

*Referential Composition

[1)]IRGANOX L57 (alkylated diphenyl amine antioxidant):

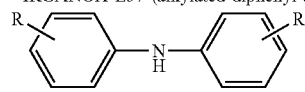

one of R and R' hydrogen, the other one tert-butyl or octyl; or both R and R' tert-butyl or octyl

[2)]IRGAMET 39 (tolutriazol based metal deactivator):

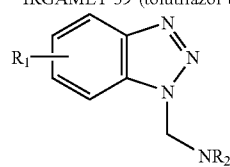

[3)]IRGANOX L135 (liquid ester type phenolic antioxidant):

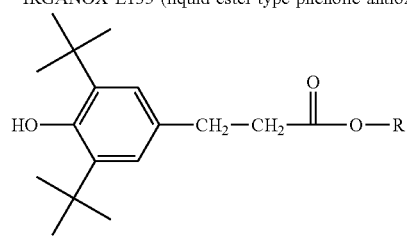

[4)]IRGANOX 1035 (solid dimeric sulphur-containing ester type phenolic antioxidant):

[structure: HO-[3,5-di-tert-butyl-phenyl]-CH₂-CH₂-C(=O)-O-CH₂-CH₂-S, bracketed ×2]

[4)]IRGANOX 1300:

[structure: HO-[3,5-di-tert-butyl-phenyl]-CH₂-CH₂-C(=O)-O-CH₃]

There is no significant corrosion of any of the metal test specimen tested. Referential Test Compositions 2 and 3, which contain 0.3% and 0.138% of the phenolic sulphur-containing antioxidant IRGANOX 1035, produce higher amounts of sludge. The amount of sludge is low in the test compositions according to Examples 1 and 2, which are based either on a mixture (Example 1) or one (Example 2) phenolic antioxidant(s) of the formula I.

3.2 Deposit Test

The Hot Tube Test is an analysis of lubricant effect on diesel engine scuffing according to S. Ohkawa, et al., *SAE Technical Paper Series*, 840262, Detroit/USA 1984. An assessment of piston deposits, oxidation and detergency effects associated with an oil formulation is made by slowly feeding the oil together with compressed air through a heated glass capillary tube. The oil flows through the hot glass capillary tube while wetting the inner wall of the tube and forming lacquer. Tests are run for 16 h at a temperature of 248° C. At the conclusion of the test, the tubes are washed and rated for cleanliness. A scale of 0–10 is used to rate the tubes with 10 being completely clean and 0 being completely blackened. The results are reported in Table 2.

3.2 Oxidation Test HPDSC High-pressure differential scanning calorimetry (HPDSC) is used to determine the oxidation stability of oil formulations and additives. A small quantity of formulated oil in an aluminium pan is placed in a test cell, which is pressurised with oxygen to 150 psi. The cell is heated to a 190° C. and held at that temperature until an exothermic reaction occurs. The extrapolated onset time is determined and reported as the oxidation induction time for the formulation. The results are reported in Table 2.

3.3 Viscosity Increase Test (Ciba Viscosity Increase Test, CVIT)

In the test according to G. A. Mazzamaro, et al., *SAE Technical Paper Series*, 940793, Detroit/USA 1994 a formulated oil containing additives is mixed with hydroperoxide and soluble iron catalysts. The mixture is heated to 140° C. in a glass tube and oxygen is blown through the oil at a flow rate of 5 l per hour. Samples are taken periodically for viscosity measurements. The time period to achieve a 375% viscosity increase is determined as a measure of the oxidative stability of the sample. The results are reported in Table 2.

TABLE 2

| | AO Composition Tested | | | | | |
|---|---|---|---|---|---|---|
| | Test Composition 1 | Test Composition 2 | Ref. 1* | Ref. 2* | Ref. 3* | Ref. 4* |
| Components | | | | | | |
| MTX-1[2)] | Balance | Balance | 100 | Balance | Balance | Balance |
| Example 1 | 1.0 | | | | | |
| Example 2 | | 1.0 | | | | |
| IRGANOX L135[3)] | | | | 1.0 | | 0.41 |
| IRGANOX 1035[4)] | | | | | 1.0 | 0.49 |
| IRGANOX 1300[5)] | | | | | | 0.10 |
| Results | | | | | | |
| Hot Tube Deposit Test [rating] | 5/4.5 | 5/4 | 3/3 | 4/4.5 | 4/5 | 3.5/4 |
| HPDSC, induction time [min] | 68/71 | 54/54 | 33/30 | 52/53 | 61/62 | 56/53 |
| VIT [h] | 110/102 | 79/88 | 33/33 | 74/75 | 124/114 | 98/98 |

*Referential Composition
[2)]MTX-1 is a SAE 30 CE quality level heavy-duty diesel base formulation. It contains dispersant, detergent, antiwear and antifoam additives but no supplemental antioxidant.
[3)]IRGANOX L135: see Table 1
[4)]IRGANOX 1035: see Table 2
[5)]IRGANOX 1300: see Table 3

There are some improvements over the base formulation, referential formulation 1, as shown by the Test Compositions 1 and 2 in the various tests. The test compositions are, in general, more efficient and perform better than the Referential Compositions 2, 3 and 4.

The invention claimed is:
1. A product obtained by reacting
a) At least one compound of formula (I)

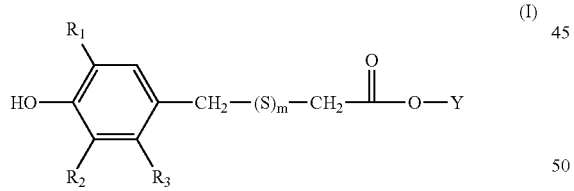

(I)

wherein
one of $R_1$ and $R_2$ independently of one another represents hydrogen or a substituent selected from the group consisting of $C_1$–$C_{18}$alkyl, phenyl, $(C_1$–$C_4$alkyl$)_{1-3}$phenyl, phenyl-$C_1$–$C_3$alkyl, $(C_1$–$C_4$alkyl$)_{1-3}$phenyl-$C_1$–$C_3$alkyl, $C_5$–$C_{12}$cycloalkyl and $(C_1$–$C_4$alkyl$)_{1-3}$$C_5$–$C_{12}$cycloalkyl;
and the other one represents a substituent selected from the group consisting of $C_1$–$C_{18}$alkyl, phenyl, $(C_1$–$C_4$alkyl$)_{1-3}$phenyl, phenyl-$C_1$–$C_3$alkyl, $(C_1$–$C_4$alkyl$)_{1-3}$phenyl-$C_1$–$C_3$alkyl, $C_5$–$C_{12}$cycloalkyl and $(C_1$–$C_4$alkyl$)_{1-3}$$C_5$–$C_{12}$cycloalkyl;
$R_3$ represents hydrogen or methyl;
Y represents hydrogen or $C_1$–$C_6$alkyl; and
m represents zero or 1; with b) At least one compound of formula (II)

$$R_4\text{—OH} \quad \text{(II)}$$

wherein $R_4$ represents $C_4$–$C_{25}$alkyl; and
c) At least one compound of formula (III)

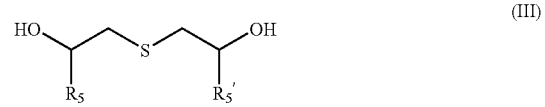

(III)

wherein $R_5$ and $R_5'$ independently of one another represent hydrogen or $C_1$–$C_6$alkyl.

2. A product according to claim 1, obtained by reacting
a) At least one compound of formula (I) wherein one of $R_1$ and $R_2$ represents methyl or tert-butyl and the other one of $R_1$ and $R_2$ represents tert-butyl; $R_3$ represents hydrogen; Y represents $C_1$–$C_6$alkyl; and m represents zero or one; and
b) At least one compound of formula (II) wherein $R_4$ represents $C_4$–$C_{18}$alkyl; and
c) At least one compound of formula (III) wherein $R_5$ and $R_5'$ represent hydrogen.

3. A product according to claim 1, obtained by reacting
a) At least one compound of formula (I) wherein one of $R_1$ and $R_2$ represents methyl or tert-butyl and the other one of $R_1$ and $R_2$ represents tert-butyl; $R_3$ represents hydrogen; Y represents methyl and m represents zero; and
b) At least one compound of formula (II) wherein $R_4$ represents $C_4$–$C_{18}$alkyl; and
c) At least one compound of formula (III) wherein $R_5$ and $R_5'$ represent hydrogen.

4. A product according to claim 1, obtained by reacting
a) A mixture comprising a compound of formula (I) wherein $R_1$ and $R_2$ represent tert-butyl; $R_3$ represents hydrogen; Y represents methyl and m represents zero; and
A compound of formula (I) wherein one of $R_1$ and $R_2$ represents methyl and the other one tert-butyl; $R_3$ represents hydrogen; Y represents methyl and m represents zero; and
b) At least one compound of formula (II) wherein $R_4$ represents $C\text{-}C_{18}$alkyl; and
c) At least one compound of formula (III) wherein $R_5$ and $R_5'$ represent hydrogen.

5. A composition comprising
A) A product according to claim 1; and
B) A functional fluid subject to oxidative, thermal or light induced degradation.

6. A composition comprising
A) A product according to claim 1; and
B) A base oil of lubricating viscosity.

7. A process for preparing a liquid mixture of phenolic sulphur-containing antioxidants, which process comprises reacting
a) At least one compound of formula (I)

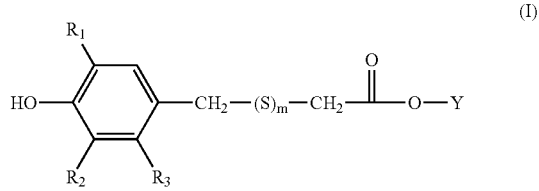

wherein
one of $R_1$ and $R_2$ independently of one another represents hydrogen or a substituent selected from the group consisting of $C_1\text{–}C_{18}$alkyl, phenyl, $(C_1\text{–}C_4\text{alkyl})_{1\text{-}3}$phenyl, phenyl-$C_1\text{–}C_3$alkyl, $(C_1\text{–}C_4\text{alkyl})_{1\text{-}3}$phenyl-$C_1\text{–}C_3$alkyl, $C_5\text{–}C_{12}$cycloalkyl and $(C_1\text{–}C_4\text{alkyl})_{1\text{-}3}$$C_5\text{–}C_{12}$cycloalkyl;
and the other one represents a substituent selected from the group consisting of $C_1\text{–}C_{18}$alkyl, phenyl, $(C_1\text{–}C_4\text{alkyl})_{1\text{-}3}$phenyl, phenyl-$C_1\text{–}C_3$alkyl, $(C_1\text{–}C_4\text{alkyl})_{1\text{-}3}$phenyl-$C_1\text{–}C_3$alkyl, $C_5\text{–}C_{12}$cycloalkyl and $(C_1\text{–}C_4\text{alkyl})_{1\text{-}3}$$C_5\text{–}C_{12}$cycloalkyl;
$R_3$ represents hydrogen or methyl;
Y represents hydrogen or $C_1\text{–}C_6$alkyl; and
m represents zero or 1; with
b) At least one compound of formula (II)

wherein $R_4$ represents $C_4\text{–}C_{25}$alkyl; and c) At least one compound of formula (III)

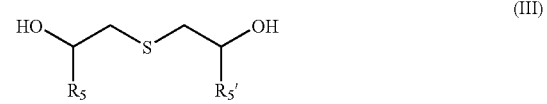

wherein $R_5$ and $R_5'$ independently of one another represent hydrogen or $C_1\text{–}C_6$alkyl.

8. A process for stabilising a composition of matter subject to oxidative, thermal or light induced degradation, which comprises adding to said composition of matter at least one product according to claim 1.

9. A process according to claim 7, which process comprises reacting
a) At least one compound of formula (I) wherein one of $R_1$ and $R_2$ represents methyl or tert-butyl and the other one of $R_1$ and $R_2$ represents tert-butyl; $R_3$ represents hydrogen; Y represents $C_1\text{–}C_6$alkyl; and m represents zero or one; and
b) At least one compound of formula (II) wherein $R_4$ represents $C_4\text{–}C_{18}$alkyl; and
c) At least one compound of formula (III) wherein $R_5$ and $R_5'$ represent hydrogen.

10. A process according to claim 7, which process comprises reacting
a) At least one compound of formula (I) wherein one of $R_1$ and $R_2$ represents methyl or tert-butyl and the other one of $R_1$ and $R_2$ represents tert-butyl; $R_3$ represents hydrogen; Y represents methyl and m represents zero; and
b) At least one compound of formula (II) wherein $R_4$ represents $C_4\text{–}C_{18}$alkyl; and
c) At least one compound of formula (III) wherein $R_5$ and $R_5'$ represent hydrogen.

11. A process according to claim 7, which process comprises reacting
a) A mixture comprising a compound of formula (I) wherein $R_1$ and $R_2$ represent tert-butyl; $R_3$ represents hydrogen; Y represents methyl and m represents zero; and
A compound of formula (I) wherein one of $R_1$ and $R_2$ represents methyl and the other one tert-butyl; $R_3$ represents hydrogen; Y represents methyl and m represents zero; and
b) At least one compound of formula (II) wherein $R_4$ represents $C\text{-}C_{18}$alkyl; and
c) At least one compound of formula (III) wherein $R_5$ and $R_5'$ represent hydrogen.

* * * * *